US007972835B2

(12) United States Patent
Hitosugi et al.

(10) Patent No.: US 7,972,835 B2
(45) Date of Patent: Jul. 5, 2011

(54) BLOOD-VISCOSITY REDUCING AGENT

(75) Inventors: Masahito Hitosugi, Tochigi (JP); Hiroaki Maeda, Tokyo (JP); Kazunobu Omura, Tokyo (JP)

(73) Assignees: Daiwa Pharmaceutical Co., Ltd., Tokyo (JP); Masahito Hitosugi, Tochigi (JP)

( * ) Notice: Subject to any disclaimer, the term of this patent is extended or adjusted under 35 U.S.C. 154(b) by 169 days.

(21) Appl. No.: 12/369,329

(22) Filed: Feb. 11, 2009

(65) Prior Publication Data
US 2009/0202982 A1 Aug. 13, 2009

Related U.S. Application Data

(62) Division of application No. 11/093,373, filed on Mar. 29, 2005, now abandoned.

(30) Foreign Application Priority Data

Nov. 16, 2004 (JP) ................................. 2004-331559

(51) Int. Cl.
*C12N 1/20* (2006.01)
*C12N 9/56* (2006.01)
*A01N 1/02* (2006.01)
*A61K 9/36* (2006.01)

(52) U.S. Cl. ........ 435/252.31; 435/2; 435/222; 424/780
(58) Field of Classification Search .................. None
See application file for complete search history.

(56) References Cited

U.S. PATENT DOCUMENTS

| | | | |
|---|---|---|---|
| 6,395,889 B1 | 5/2002 | Robison | |
| 6,730,504 B2 * | 5/2004 | Takaoka | 435/183 |
| 6,866,851 B1 * | 3/2005 | Milbrandt et al. | 424/192.1 |
| 7,098,029 B1 | 8/2006 | Belyea et al. | |
| 7,795,222 B2 * | 9/2010 | Nishida et al. | 514/1.1 |
| 7,795,385 B2 * | 9/2010 | Schwartsmann et al. | 530/309 |
| 2001/0046697 A1 * | 11/2001 | Takaoka | 435/252.31 |
| 2002/0146786 A1 * | 10/2002 | Takaoka | 435/148 |
| 2004/0043014 A1 | 3/2004 | Moriyama et al. | |
| 2004/0209333 A1 * | 10/2004 | Takaoka | 435/133 |

FOREIGN PATENT DOCUMENTS

| | | |
|---|---|---|
| JP | 61-162184 | 7/1986 |
| JP | 1-180834 | 7/1989 |
| JP | 3-168082 | 7/1991 |
| JP | 6-153977 | 6/1994 |
| JP | 8-208512 | 8/1996 |
| JP | 2001-352929 | 12/2001 |

OTHER PUBLICATIONS

Choi, Nack-Shick et al., "Purification and characterization of a new peptidase, bacillopeptidase DJ-2 having fibrinolytic activity: Produced by *Bacillus* sp DJ-2 form Doen-Jang," Journal of Microbiology and Biotechnology, Feb. 2005, 15(1), pp. 72-79.

Hitosugi, et al., "Rheologic Changes in Venous Blood During Prolonged Sitting," Thrombosis Research, 2000, 100, pp. 409-412.
Hitosugi, et al., "Change in Blood Viscosity by Heparin and Argatroban," Thrombosis Research, 2001, 104, pp. 371-374.
Hitosugi, et al., "Change in Blood Viscosity with Synthetic Protease Inhibitors," Journal of Pharmacological Sciences, 2003, 91, pp. 334-336.
Hitosugi, et al., "Changes in Blood Viscosity with Mucopolysaccharide Polysulfate," Journal of Pharmacological Sciences, 2004, 95, pp. 132-134.
Omura, Kazonobu et al., "Fibrinolytic and anti-thrombotic effect of NKCP, the protein layer from *Bacillus subtilis* (natto)," Biofactors, Jan. 11, 2005, 22(1-4), pp. 185-187.
Sloma, A., et al., "*Bacillopeptidase F* of *Bacillus subtilis*: purification of the protein and cloning of the gene," J. Bacteriol., 1990, 172, pp. 5520-5521.
Sloma, et al., "Cloning and Characterization of the Gene for an Additional Extracellular Serine Protease of *Bacillus Subtilis*," Journal of Bacteriology, Nov. 1991, 173(21), pp. 6889-6895.
Wu, et al., "Cloning, Genetic Organization, and Characterization of a Structural Gene Encoding *Bacillopeptidase F* from *Bacillus Subtilis*," The Journal of Biological Chemistry, 1990, 265(12), pp. 6845-6850.
Yamagata, Y., et al., "Molecular cloning and nucleotide sequence of the 90k serine protease gene, hspK, from *Bacillus subtilis* (natto) No. 16," Current Microbiology, Dec. 1995, 31(6), pp. 340-344.

* cited by examiner

*Primary Examiner* — Christopher R. Tate
*Assistant Examiner* — Aaron Kosar
(74) *Attorney, Agent, or Firm* — Blakely, Sokoloff, Taylor & Zafman LLP

(57) ABSTRACT

A blood-viscosity reducing agent contains a protein derived from *Bacillus subtilis* natto and including, sequentially from an amino group terminal, a first structural amino acid sequence having alanine, threonine, aspartic acid, glycine, valine, glutamic acid, tryptophan, asparagine, valine, aspartic acid, glutamine, isoleucine, aspartic acid, alanine, proline, lysine, alanine, tryptophan, alanine, leucine, glycine, tyrosine aspartic, acid, glycine, threonine, glycine, threonine, valine, valine, alanine, serine, isoleucine, aspartic acid, threonine, glycine, valine, glutamic acid, tryptophan, asparagine, histidine, proline, alanine, leucine, lysine, glutamic acid, lysine, tyrosine, arginine, glycine, tyrosine, asparagine, proline, glutamic acid, asparagine, proline, asparagine, glutamic acid, proline, glutamic acid, asparagine, glutamic acid, methionine, asparagine, tryptophan, tyrosine, aspartic acid, alanine, valine, alanine, glycine, glutamic acid, alanine, serine, proline, tyrosine, aspartic acid, aspartic acid, leucine, alanine, histidine, glycine, threonine, histidine, valine, and threonine, a second structural amino acid sequence having alanine, phenylalanine, serine, glutamic acid, aspartic acid, glycine, glycine, threonine, aspartic acid, alanine, aspartic acid, isoleucine, leucine, glutamic acid, alanine, glycine, glutamic acid, tryptophan, valine, and leucine, a third structural amino acid sequence having aspartic acid, alanine, glutamic acid, glycine, asparagine, proline, histidine, proline, glutamic acid, methionine, alanine, proline, aspartic acid, and valine, and a fourth structural amino acid sequence having valine, proline, glycine, glutamine, alanine, tyrosine, glutamic acid, aspartic acid, glycine, tryptophan, and aspartic acid, thereby reducing the viscosity of whole blood.

2 Claims, 1 Drawing Sheet

FIG. 1 CHANGE BLOOD VISCOSITY
 #: DIFFERENCE FROM BASELINE BY DUNCAN'S MULTIPLE TEST, P<0.05
 *: DIFFERENCE BETWEEN NKCP VS. PLACEBO BY PAIRED T TEST, P<0.05

US 7,972,835 B2

BLOOD-VISCOSITY REDUCING AGENT

CROSS-REFERENCE TO RELATED APPLICATIONS

This application is a divisional application of U.S. application Ser. No. 11/093,373 filed Mar. 29, 2005.

SEQUENCE LISTING

A computer readable form copy of the Sequence Listing entitled "P482D_SeqList.txt" is herein incorporated by reference. This Sequence Listing consists of [SEQ. ID NOs:1-5].

BACKGROUND OF THE INVENTION

The present invention relates to a blood-viscosity reducing agent which reduces the viscosity of whole blood.

Natto has been Japanese traditional fermented food taken from the 1600s to the present for a long period of time and is excellent as food which allows Japanese to ingest soy protein efficiently. For example, natto has a higher digestibility than soy beans. This is because the protein, fat, starch, and the like as the main ingredients of soy beans are decomposed into an amino acid, fatty acid, and glucose by Bacillus subtilis natto, and digestibility upon ingestion is enhanced.

Most of the vitamin B family contained in natto smoothes physical functions and shortens fatigue recovery. Natto contains a large amount of vitamin $B_2$ and is expected for recovery of asthenopia. The content of vitamin K in natto is the highest among the foodstuffs. Natto can be expected to improve blood calcium metabolism, e.g., to prevent osteoporosis and improve the blood clotting ability.

In recent years, a variety of functions of natto have been clarified, and natto's effects have received a great deal of attention as health food. The consumption of natto has been increasing. Particularly, the natto-containing enzyme called Nattokinase is effective as fibrinolytic and thrombolytic agents, as the production methods, physicochemical nature, and biochemical nature are disclosed in Japanese Patent Laid-Open Nos. 61-162184 (reference 1), 3-168082 (reference 2), and 6-153977 (reference 3).

Nattokinase has received a great deal of attention as a thrombolytic agent or thrombogenesis inhibitor, as described in Japanese Patent Laid-Open Nos. 1-180834 (reference 4) and 8-208512 (reference 5). These references disclose techniques associated with safe, easily accessible agents containing Nattokinase as the active ingredient in place of agents, i.e., a thrombolytic agent and platelet aggregation inhibitor such as urokinase, streptokinase, and a tissue plasminogen activator, which are currently used for thrombus in the clinical field.

Japanese Patent Laid-Open No. 2001-352929 (reference 6) discloses natto's processed food produced in the following manner. In a state wherein flavour unique to fermented natto is absent, the active ingredient unique to natto is extracted from a dialyzed medium in which soy protein powder purified from soy beans is cultured with Bacillus subtilis natto. According to the proposal of reference 6, the use of this processed food allows to delay blood clotting time and suppress thrombogenesis in addition to the thrombolytic effect using Nattokinase.

As described above, the product derived from natto has various effects such as the delay of blood clotting time and suppression of thrombogenesis in addition to the thrombolytic effect. The present inventors found a new function other than the above effects in the natto's processed food disclosed in reference 6.

SUMMARY OF THE INVENTION

It is an object of the present invention to provide an agent having a new function by using a product derived from natto.

In order to achieve the above object of the present invention, there is provided a blood-viscosity reducing agent essentially consisting of a protein derived from Bacillus subtilis natto and including, sequentially from an amino terminal, a first structural amino acid sequence having alanine, threonine, aspartic acid, glycine, valine, glutamic acid, tryptophan, asparagine, valine, aspartic acid, glutamine, isoleucine, aspartic acid, alanine, proline, lysine, alanine, tryptophan, alanine, leucine, glycine, throsine, aspartic acid, glycine, threonine, glycine, threonine, valine, valine, alanine, serine, isoleucine, aspartic acid, threonine, glycine, valine, glutamic acid, tryptophan, asparagine, histidine, proline, alanine, leucine, lysine, glutamic acid, lysine, throsine, arginine, glycine, tyrosine, asparagine, proline, glutamic acid, asparagine, proline, asparagine, glutamic acid, proline, glutamic acid, asparagine, glutamic acid, methionine, asparagine, tryptophan, throsine, aspartic acid, alanine, valine, alanine, glycine, glutamic acid, alanine, serine, proline, tyrosine, aspartic acid, aspartic acid, leucine, alanine, histidine, glycine, threonine, histidine, valine, and threonine, a second structural amino acid sequence having alanine, phenylalanine, serine, glutamic acid, aspartic acid, glycine, glycine, threonine, aspartic acid, alanine, aspartic acid, isoleucine, leucine, glutamic acid, alanine, glycine, glutamic acid, tryptophan, valine, and leucine, a third structural amino acid sequence having aspartic acid, alanine, glutamic acid, glycine, asparagine, proline, histidine, proline, glutamic acid, methionine, alanine, proline, aspartic acid, and valine, and a fourth structural amino acid sequence having valine, proline, glycine, glutamine, alanine, tyrosine, glutamic acid, aspartic acid, glycine, tryptophan, and aspartic acid, thereby reducing the viscosity of whole blood.

DESCRIPTION OF THE PREFERRED EMBODIMENT

Figure 1:
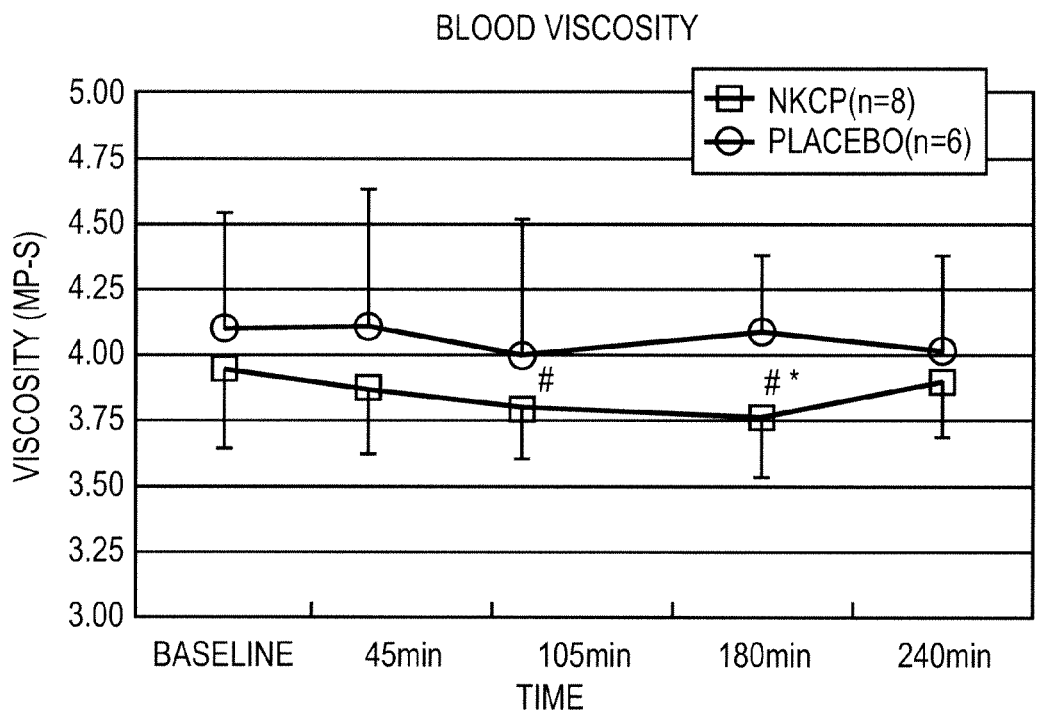
FIG. 1 is a graph showing the measurement result of blood viscosity.

An embodiment of the present invention will be described with reference to the accompanying drawings. The present inventors have developed as processed food a product (to be referred to as an NKCP hereinafter) obtained by efficiently purifying a fibrinolytic substance from a soy bean liquid medium of Bacillus subtilis natto cultivation. During this development, the present inventors have obtained a new finding as a blood-viscosity reducing effect in the study process of a natto's fibrinolytic activity as a dissolving blood clot.

The NKCP production will be described below. Bacillus subtilis natto (Takahashi strain) is added to pure water and stirred to prepare a suspension. A small amount of suspension is inoculated to the plate agar prepared by using the standard agar medium. The suspension is cultured at 37° C. for 24 hrs to obtain a colony of Bacillus subtilis natto on the plate agar.

Two-hundred mL of a liquid medium containing 1 g of glycose and 4 g of soy protein powder as the materials are prepared in an Erlenmeyer flask having an internal volume of 500 mL. The flask is held in an autoclave at 120° C. for 30 min to sterilize the interior of the Erlenmeyer flask. The soy protein powder is purified from soy beans. A soy bean powder obtained by grinding soy beans can be used as the material. It suffices that soy protein is contained in the material.

*Bacillus subtilis* natto is sampled once with an inoculating loop having a diameter of 2 mm from the colony of *Bacillus subtilis* natto cultured on the plate agar. The sampled *Bacillus subtilis* natto is inoculated on the liquid medium in the Erlenmeyer flask. The Erlenmeyer flask containing the liquid medium on which the *Bacillus subtilis* natto is inoculated is kept open at 40° C. and is rotated and vibrated for two days to incubate the liquid medium in the Erlenmeyer flask.

Twenty L of a liquid medium containing 100 g of glucose, 400 g of soy protein powder, and a soluble starch are prepared in a jar fermenter having an internal volume of 30 L, thereby sterilizing the liquid medium. In addition, 200 mL of the *Bacillus subtilis* natto medium incubated in the Erlenmeyer flask are added to the liquid medium in the jar fermenter. The resultant medium is incubated while being bubbled and stirred at 42° C. for two days. Three other identical media are prepared to obtain about 50 L of the soy protein liquid medium.

The bodies of *Bacillus subtilis* natto and impurities are centrifugally removed from the resultant soy protein liquid medium, and 1 mol of ammonium sulfate is added to it. The addition of ammonium sulfate facilitates coagulation by making hydrophobic nature of proteins including high molecular compounds such as a variety of enzymes dispersed in the fermented solution. The addition of ammonium sulfate produces new insoluble substances. These substances are filtered with glass fiber filter paper.

A hydrophobic chromatography resin equilibrated by a 1-mol ammonium sulfate solution is dipped in the filtered resultant soy protein liquid medium. Hydrophobic high molecular compounds are coagulated (attached) on the resin. The compounds on the resin are dipped in a 0.1-mol ammonium bicarbonate solution to elute the high molecular compounds attached to the resin, thereby obtaining 40 L of a condensed liquid medium.

The condensed liquid medium is ultrafiltered using an ultrafiltration membrane having a preparation scale M.W. of 10,000 to separate low-molecular weight substances. The condensed liquid medium is condensed from 40 L to 10 L. Ten L of pure water is added to the condensate obtained through the ultrafiltration membrane to obtain a 20-L solution. The resultant solution is repeatedly condensed three times until the volume becomes 10 L by separating the low-molecular weight substances. By this three-time condensation, a fermented soy protein liquid medium which almost all low-molecular weight substances are eliminated can be prepared.

The main components of flavour unique to fermented natto are low-molecular compounds such as dimethylpyrazine (molecular weight: 108.14), trimethylpyrazine (molecular weight: 122.17), tetramethylpyrazine (molecular weight: 126.20), 2-methyl butyrate (molecular weight: 102.13), isovaleric acid (molecular weight: 102.13), and ammonia (molecular weight: 17.03). Vitamin K2 contained in natto is a hydrocarbon compound having a molecular weight of 649. On the other hand, proteins such as an enzyme (e.g., Nattokinase) are polymer compounds having molecular weights of several ten-thousands or more.

By removing the low-molecular substances by ultrafiltration, almost all the low-molecular substances such as the "flavour" components unique to fermented natto and vitamin $K_2$ can be removed from the fermented soy protein liquid medium. Finally, 2 kg of lactose as a diluent are added to the fermented soy protein liquid medium which the low-molecular substances are removed by the ultrafiltration, and the resultant solution was freeze-dried to prepare about 2.1 kg of soy protein ferment powder (NKCP).

Since around 1990, Nattokinase serving as a fibrinolytic substance originated from natto has been reported as Subtilisin (alkaline protease). The main active substance of NKCP prepared as described above is purified, and examined by various equipment analyses. The analysis results exhibited that the main active substance is 34,000-dalton Bacillopeptidase F serving as one of the enzymes secreted by *Bacillus subtilis* natto, and is different from the former Nattokinase.

In order to set the standards as NKCP functional food, a quantitative analysis was conducted by preparing the following measurement kit in addition to the conventional substitute index called stroma decomposition activity. The kit was prepared by the enzyme-linked immunosorbent assay (ELISA) upon preparing an antibody of 34,000-dalton Bacillopeptidase F. These analysis methods have been confirmed to be appropriate for a quantitative analysis method upon Japan food research laboratories Inc.

In order to develop NKCP as functional food, safety and efficacy were examined in various animal experiments and human clinical tests. As for safety, the finding met the level of food for specified health uses with a claim accepted by the Ministry of Health, Labour and Welfare, and no clinical problem was observed within the clinical dosage. The efficacy expected for fibrinolytic activity was confirmed in both various animal experiments and various human clinical tests. In the process of these experiments and tests, not only fibrinolytic activity for thrombus, which had been formerly reported of Subtilisin, but also the action for suppressing thrombogenesis and decreasing the blood viscosity could be found in NKCP.

The confirmation for the action for decreasing the blood viscosity in an anticoagulant containing NKCP of this embodiment will be described below. Fresh blood was collected from volunteers with property of nonsmoking, prior informed consent, and 20 to 22 years old. The fresh blood of immediately after collection was poured in a measurement vessel in which an oscillation viscometer was kept at 37.degree. C. The clinical test values and blood viscosity values of the blood were measured over time at a shear rate of 400 to 500 mPaS.

The sample was dissolved in normal saline and a sample of ¹/₁₀₀ of the amount of the blood was added in the measurement vessel upon the poured fresh blood. The fresh blood was quickly stirred with the sample in the process of viscosity measurement. Blood was collected carefully without stimulating the coagulation/fibrinolytic system. The blood was treated that its coagulation could be observed in the oscillation viscometer.

The viscosity of the human blood measured by the above method can be observed without anticoagulants or diluent at a physiological temperature while ensuring the physical change as if the blood were flowing in an actual human body. The blood viscosity exhibits the balanced state immediately after the blood placed in the measurement system. The viscosity increases exponentially about 300 sec after the balanced state on the basis of the blood coagulation reaction. See references 7, 8, and 9 for further details.

In another blood viscosity measurement equipment such as an MC-FAN (Micro Channel array Flow ANalyzer), measurement is performed with an anticoagulant in order to prevent blood coagulation in the equipment. This suffices when the blood viscosity associated with adhesion and deformation of blood cells (mostly blood erythrocytic cells) in the blood is measured. However, an oscillation viscometer is better than the above equipment in measurement under living body condition including coagulation and fibrinolysis of the blood.

The exponential increase timing of the viscosity is delayed when blood is added to NKCP in an amount of 0.05 mg/mL or more. The increase in viscosity is not confirmed in an amount of 0.5 mg/mL or more. The balanced viscosity was decreased about 10% in an amount of 0.25 mg/mL and about 20% in an amount of 0.5 mg/mL. The degree of symptom of coagulation and expression timing in addition of blood in NKCP are different from the addition of a tissue plasminogen activator serving as a thrombolytic agent or Heparin serving as an anticoagulant.

The blood viscosity in a clinical condition upon ingesting NKCP is measured. Eight adult subjects with prior informed consent. Six other subjects are selected as a placebo-treated control group. In selecting subjects, persons obviously suffering acute diseases and acute exacerbation of chronic diseases are excluded from the subjects.

The dose per day is 10 tablets, which is equivalent to 1,250 mg of NKCP. In the first day of study, 10 tablets are administered with two rice balls in the morning. From the second day, 10 tablets are administered once per day after the dinner for a week. In the first day of study, the blood viscosities are measured before administration, and 105 min, 180 min, and 240 min after the administration.

The blood viscosity is measured at the shear rate of 400 to 500 mPas in the measurement vessel in which all blood samples are kept at 37.degree. C. of the oscillation viscometer in the same manner as described above. The change in blood viscosity is determined using the "balanced viscosity" set before the exponential change in viscosity. As shown in Table 1 and FIG. 1, the decreases in blood viscosity are observed in 180 min and 240 min, while no change in blood viscosity is observed in the placebo-treated group.

As for the blood viscosity measurements, see Masahito Hitosugi, et al., "Rheologic Changes in Venous Blood During Prolonged Sitting", Thrombosis Research 100, pp. 409-412, 2000 (reference 7), Masahito Hitosugi, et al., "Change in Blood Viscosity by Heparin and Argatroban", Thrombosis Research 104, pp. 371-374, 2001 (reference 8), and Masahito Hitosugi, et al., "Change in Blood Viscosity with Synthetic Protease Inhibitors", Journal of Pharmacological Sciences, Vol. 91, pp. 334-336, 2003 (reference 9).

As described above, according to the blood-viscosity reducing agent containing NKCP of this embodiment, the blood viscosity obviously reduces. The blood-viscosity reducing action is expected to contribute to improvements for health care and welfare of mankind such as prevention of hemostasis serving as an inducer for thrombosis, improvement of the active capacity in the peripheral tissue such as muscles concerning with increases in supplying oxygen and nutrients, improvement of hypertension along with the decrease of peripheral blood vessel resistance, prevention of arteriosclerosis progression and improvement of the conditions of heart failure caused by a decrease of peripheral blood vessel resistance.

The blood-viscosity reducing agent has properties for preventing an increase in blood viscosity and its coagulation after blood collection, which poses problems in clinical tests using sampling blood, and for improving clinical test precision and convenience. The blood-viscosity reducing agent is also expected to improve the cleaning effect due to suppression of the viscosity rise in blood pollution of tools used in clinical examinations and treatments. The blood-viscosity reducing agent may contribute to maintenance and reservation of tissue subjected to treatment and surgical operation, and tissue erased from a living body and blood collected from it.

The research result of physiochemical nature of NKCP serving as the blood-viscosity reducing agent according to this embodiment described above will be described below. The gene sequence of Bacillus subtilis natto (Takahashi strain) serving as a strain for producing NKCP is analyzed by the "method of nucleotide sequence of 16S ribosomal DNA" to exhibit 168 Bacillus subtilis subsp, Subtilis strains and 99.9% or more homology.

TABLE 1

Change parameters after NKCP administration with time

|  | Pre | 45 min | 105 min | 180 min | 240 min |
| --- | --- | --- | --- | --- | --- |
| NKCP(n = 8) | 3.93 ± 0.283 | 3.86 ± 0.243 | 3.80 ± 0.193 | 3.79 ± 0.244 | 3.89 ± 0.205 |
| Placebo(n = 6) | 4.10 ± 0.444 | 4.11 ± 0.528 | 4.00 ± 0.513 | 4.09 ± 0.298 | 4.02 ± 0.359 |

Values are mean ± SD of 8 volunteers. Difference from pre administration, Duncan's Multiple Test,
*p < 0.05,
**p < 0.01.
VIS: blood viscosity at 32° C. (mPa · s),
Ht: hematocrit (39.8-51.8%)

Figure 2:
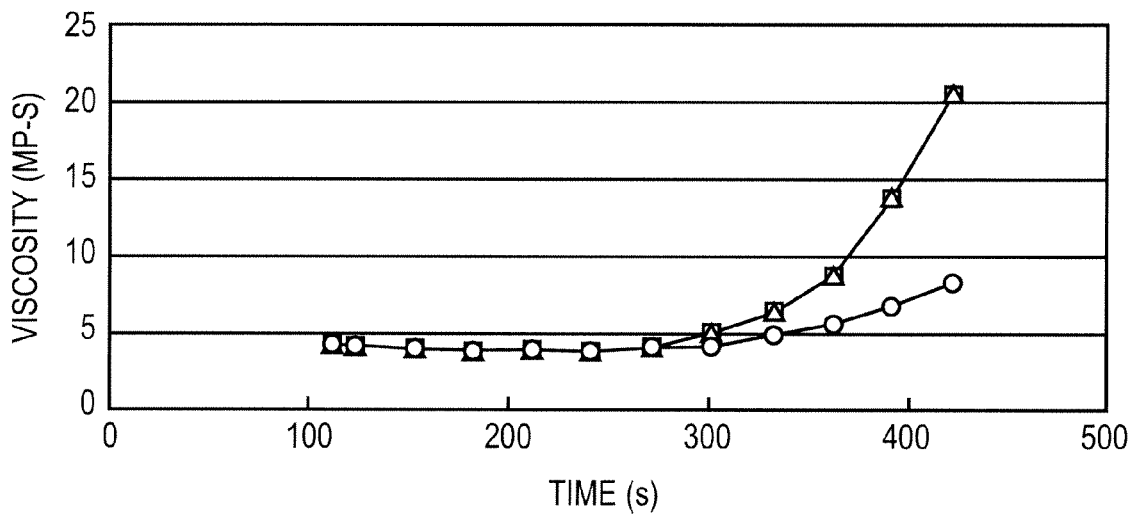
FIG. 2 is a graph showing the measurement result of blood viscosity.

The viscosities of blood added with NKCP, blood added with another Nattokinase, and blood with no additive are measured using the oscillation viscometer. Changes in FIG. 2 are confirmed. In FIG. 2, the measurement results of the blood added with NKCP, the blood added with another Nattokinase, and the blood with no additive are represented by a dot, black square, and black triangle, respectively. The measurement result of the blood added with NKCP, represented by the dot, exhibits that the viscosity increases less than the blood with another Nattokinase. Therefore, the change in blood viscosity is not essentially observed in the enzyme and protein contained in natto.

The molecular weight of NKCP is measured by TOF-MS (Time Of Flight Mass Spectrometry) to be 34, 134 daltons. The molecular weight of NKCP is assigned to be about 34,100 daltons. For this measurement, NKCP sample is repeatedly purified by gravitational chromatograms using a molecular sieve carrier sold under the trademark TOYOPEARL. Samples purified in the same manner as described above are used in the subsequent measurements.

The NKCP structure is analyzed by an automatic amino acid sequence analysis apparatus using the Edman degradation method to analyze 85 amino acid sequence from the amino terminal. When NKCP is limitedly degradation using Lysyl endopeptidase to obtain several peptide fragments. These peptide fragments are purified using a high-pressure liquid chromatogram. The purified fragments are subjected to mass analysis using the TOF-MF and automatic amino acid residue sequence analysis using the Edman degradation method. The resultant NKCP structure is as follows.

NKCP is confirmed to have, from the amino group terminal, structural amino acid sequences (peptide fragments) such as ATDGVEWNVDQIDAPKAWALGYDGTGTV-VASIDTGVEWNHPALKEKYRGYNPEN P NEPENEMN-WYDAVAGEASPYDDLAHGTHVT (SEQ ID NO:1) AAF-SEDGGTDADILEAGEWVL (SEQ ID NO:2), DAEGNPHPEMAPDV (SEQ ID NO:3), and VPGQAYEDGWD (SEQ ID NO:4). In other words, NKCP is a protein originated from *Bacillus subtilis* natto having the above amino acid sequences from the amino group terminal. In the above sequences, A represents alanine; G, glycine; M, methionine; S, serine; C, cystine; H, histidine; N, asparagine; T, threonine; D, aspartic acid; I, isoleucine; P, proline; V, valine; E, glutamic acid; K, lysine; Q, glutamine, W, tryptophan, F, phenylalanine; L, leucine; R, arginine; and Y, tyrosine.

From the collation of the mass analysis result and the calculation value of the molecular weight of the molecular structure, the collation with the gene database of *Bacillus Subtilis* shown in Xu-Chu, Wu, et al., "Cloning, Genetic Organization, and Characterization of a Structural Gene Encoding Bacillopeptidase F from *Bacillus Subtilis**", The Journal of Biological Chemistry Vol. 265, No. 12, pp. 6845-6850, 1990 (reference 10), and the determination result of easy biological cuttability of the amino acid sequence, NKCP is assigned to have the structural sequence (SEQ ID NO: 5)
ATDGVEWNVDQIDAPKAWALGYDGTGTVVASIDTGVEWNHPALKEKYRG

YNPENPNEPENEMNWYDAVAGEASPYDDLAHGTHVTGTMVGSEPDGTNQI

GVAPGAKWIAVKAFSEDGGTDADILEAGEWVLAPKDAEGNPHPEMAPDVV

NNSWGGGSGLDEWYRDMVNAWRAADIFPEFSAGNTDLFIPGGPGSIANP

ANYPESFATVATDINKKLADFSLQGPSPYDEIKPEISAPGVNIRSSVPGQ

AYEDGWDFTSMAGPHVSAVAALLKQANASLSVDEMEDILTSTAEPLTDST

FPDSPNNGYGHGLVNAFDAVSAVTDGLGK.

NKCP is confirmed to have the active center of Serine protease as a homologous sequence including asparagine residue, histidine residue, and serine residue. These are proven by Bacillopeptidase F serving as extracellular protease of *Bacillus subtilis*, as indicated in Alan Sloma, et al., "Cloning and Characterization of the Gene for an Additional Extracellular Serine Protease of *Bacillus Subtilis*", Journal of Bacteriology, Vol. 173, No. 21, pp. 6889-6895, Vov. 1991 (reference 11). This confirms that NKCP is one of Serine proteases.

The general physiological activity of natto, Japanese fermented traditional food, will be described. Natto has a higher digestive absorption than soy bean. This is because the protein, fat, and starch as the major components of the soy bean can be decomposed into amino acid, fatty acid, and glucose by *Bacillus subtilis* natto. Natto has a higher digestive absorption efficiency upon ingestion. Most of the vitamin B family contained in the natto smoothes physical functions and recovers the fatigue. Vitamin $B_2$ is contained in natto in a large amount and is effective to asthenopia. The content of vitamin $K_2$ in natto is the highest among the food. This can expect the improvements of calcium metabolism in the blood such as improvements in osteoporosis and blood coagulation.

In the process of decomposing the soy protein by *Bacillus subtilis* natto, various enzymes such as protease and amirase are excreted and serve as active enzyme agents to improve digestion and activate metabolism. Nattokinase can dissolve thrombus.

The difference between Nattokinase and NKCP as enzymes will be considered. Nattokinase acting as a strong fibrinolytic enzyme found in natto is a kind of a serine protease secreted from *Bacillus subtilis* natto and has a molecular weight of 20,000 daltons. Nattokinase has degradation ability of both thrombus and synthetic chromogenic substrate for plasmin. Some fibrinolytic enzymes having molecular weights of 27,000 daltons or more in addition to the above enzymes can be detected from natto.

Nattokinase serving as a new fibrinolytic enzyme having a strong fabrinolytic activity found in natto can easily be extracted from natto using normal saline. Nattokinase has a molecular weight of 20,000 daltons and an isoelectric point of 8.6. Nattokinase decomposes not only fibrin but also the synthetic chromogenic plasmine substrate. Nattokinase is relatively stable in a neutral pH and loses its activity when it is heated to 60° C.

A ten-fold normal saline is added to natto at 4° C., and the mixture is stirred and centrifugally separated. The resultant supernatant is added with 80% of ethanol to gel-filtrate. The resultant elution is condensed, and freeze-dried to prepare a crude enzyme fraction. The prepared crude enzyme fraction has some fibrinolytic enzymes having pro-ukinase activator activities. Three or more active peaks are found in a molecular weight of 27,000 daltons or more.

As described above, NKCP is a crude purified product of a fibrinolytic protein obtained from the cultured product of *Bacillus subtilis* natto. The protein derived from *Bacillus subtilis* natto having hydrolytic specificity in a Lysine-X bond obtained from NKCP contains a predetermined amount of active protein, and its molecular weight and most appropriate pH are about 34,100 daltons and 9.0, respectively. Vitamin K and body of *Bacillus subtilis* natto which causes unique flavour of fermented natto are removed from the crude purified product. This has a molecular weight different from that of Nattokinase.

The action to thrombosis and fibrinolysis system of NKCP will be described below. NKCP is confirmed to have a fibrinolytic action in vitro and in vivo. This action is more moderate than a commercially available tissue plasminogen activator (t-Pa). The action mechanism of an increase in NKCP fibrinolytic activity is caused by direct fibrin decomposition and decomposition of plasminogen activator inhibition factor 1 (PAI-1). The NKCP action mechanism is also found in a decrease in blood viscosity by measurement using an oscillation viscometer.

The examination result of the NKCP action to the coagulation thrombolytic system on a tissue culture and animal experiment is shown. The product amount of the plasminogen activator inhibition factor 1 (PAI-1) with an addition of NKCP is compared with that without any addition of NKCP using a HUVEC cell and U87-MG cell in the in vitro and in situ. The total PAI-1 produced by the HUVEC cell is 700 ng/mL for 48 hrs, and a free PAI-1 increases up to 580 ng/mL. No influence of NKCP with respect to the PAI-1 amounts is found in 0 hrs and 24 hrs.

The production amount by the U87-MG cell is completely inhibited for all incubation hours in the complete medium at a high NKCP concentration (10 μg/mL). As for the DMEM medium, the PAI-1 production is completely inhibited. When the PAI-1 products in the complete medium and DMEM medium with an addition of NKCP are compared with those without any addition of NKCP. No influence by NKCP is observed in the HUVEC cell, but low-molecular proteins increase in the U87-MG cell. This indicates that the fibrinolytic activity of NKCP is the plasminogen-activated function by the PAI-I decomposition.

When NKCP is added to blood immediately after collection and the blood viscosity is measured using an oscillation viscometer, the blood viscosity is found to be decreased. Using non-addition of the tissue plasminogen activator (t-PA), and its addition, and addition of heparin as control examples, when the 300-sec clinical test of blood, which exhibits coagulation by the oscillation viscometer, the fibrinolytic activity which is not caused by the anti-thrombosis activity and plasmine activity is found by the addition of NKCP. When a healthy adult ingests 250 mg to 500 mg of NKCP for 7 days, a decrease in blood viscosity is observed.

As described above, according to the present invention, since the above-mentioned amino acid sequence is obtained from a protein derived from *Bacillus subtilis* natto, there is provided a new agent which can decrease the blood viscosity by using the protein derived from the *Bacillus subtilis* natto as the product originated from natto.

---

The invention claimed is:

1. A method for reducing the viscosity of whole blood, comprising the steps of:
   preparing a blood-viscosity reducing agent consisting essentially of a protein produced from *Bacillus subtilis* natto, the protein comprising a molecular weight of 34,134 daltons; and
   adding the resultant blood-viscosity reducing agent directly to the whole blood in a predetermined amount to reduce the viscosity of the whole blood;
   wherein the protein consists of SEQ ID NO: 5.

2. A method for reducing the viscosity of whole blood, comprising the steps of:
   preparing a blood-viscosity reducing agent consisting essentially of a protein produced from *Bacillus subtilis* natto, the protein comprising a molecular weight of 34,134 daltons; and
   orally administering the resultant blood-viscosity reducing agent to a subject in a predetermined amount to reduce the viscosity of the whole blood of the subject; wherein the protein consists of SEQ ID NO: 5.

* * * * *

UNITED STATES PATENT AND TRADEMARK OFFICE
CERTIFICATE OF CORRECTION

| | | |
|---|---|---|
| PATENT NO. | : 7,972,835 B2 | Page 1 of 1 |
| APPLICATION NO. | : 12/369329 | |
| DATED | : July 5, 2011 | |
| INVENTOR(S) | : Masahito Hitosugi, Hiroaki Maeda and Kazunobu Omura | |

It is certified that error appears in the above-identified patent and that said Letters Patent is hereby corrected as shown below:

In the Claims, Column 13, Claim 1, lines 16-17, please delete "*Bacillus subtilis* natto" and insert --*Bacillus subtilis natto*-- so that the entire name is italicized.

In the Claims, Column 14, Claim 2, lines 15-16, please delete "*Bacillus subtilis* natto" and insert --*Bacillus subtilis natto*-- so that the entire name is italicized.

Signed and Sealed this
Twenty-eighth Day of February, 2012

David J. Kappos
*Director of the United States Patent and Trademark Office*

SEQUENCE LISTING

<160> NUMBER OF SEQ ID NOS: 5

<210> SEQ ID NO 1
<211> LENGTH: 85
<212> TYPE: PRT
<213> ORGANISM: Bacillus subtilis natto

<400> SEQUENCE: 1

```
Ala Thr Asp Gly Val Glu Trp Asn Val Asp Gln Ile Asp Ala Pro Lys
1               5                   10                  15

Ala Trp Ala Leu Gly Tyr Asp Gly Thr Gly Thr Val Val Ala Ser Ile
            20                  25                  30

Asp Thr Gly Val Glu Trp Asn His Pro Ala Leu Lys Glu Lys Tyr Arg
        35                  40                  45

Gly Tyr Asn Pro Glu Asn Pro Asn Glu Pro Glu Asn Glu Met Asn Trp
    50                  55                  60

Tyr Asp Ala Val Ala Gly Glu Ala Ser Pro Tyr Asp Asp Leu Ala His
65                  70                  75                  80

Gly Thr His Val Thr
                85
```

<210> SEQ ID NO 2
<211> LENGTH: 20
<212> TYPE: PRT
<213> ORGANISM: Bacillus subtilis natto

<400> SEQUENCE: 2

```
Ala Phe Ser Glu Asp Gly Gly Thr Asp Ala Asp Ile Leu Glu Ala Gly
1               5                   10                  15

Glu Trp Val Leu
            20
```

<210> SEQ ID NO 3
<211> LENGTH: 14
<212> TYPE: PRT
<213> ORGANISM: Bacillus subtilis natto

<400> SEQUENCE: 3

```
Asp Ala Glu Gly Asn Pro His Pro Glu Met Ala Pro Asp Val
1               5                   10
```

<210> SEQ ID NO 4
<211> LENGTH: 11
<212> TYPE: PRT
<213> ORGANISM: Bacillus subtilis natto

<400> SEQUENCE: 4

```
Val Pro Gly Gln Ala Tyr Glu Asp Gly Trp Asp
```

-continued

```
1               5                   10
```

<210> SEQ ID NO 5
<211> LENGTH: 327
<212> TYPE: PRT
<213> ORGANISM: Bacillus subtilis natto
<300> PUBLICATION INFORMATION:
<301> AUTHORS: Xu-Chu, Wu, et al.
<302> TITLE: Cloning, Genetic Organization, and Characterization of a
      Structural Gene Encoding Bacillopeptidase F from Bacillus
      Subtilis
<303> JOURNAL: The Journal of Biological Chemistry
<304> VOLUME: 265
<305> ISSUE: 12
<306> PAGES: 6845-6850
<307> DATE: 1990

<400> SEQUENCE: 5

```
Ala Thr Asp Gly Val Glu Trp Asn Val Asp Gln Ile Asp Ala Pro Lys
1               5                   10                  15

Ala Trp Ala Leu Gly Tyr Asp Gly Thr Gly Thr Val Val Ala Ser Ile
            20                  25                  30

Asp Thr Gly Val Glu Trp Asn His Pro Ala Leu Lys Glu Lys Tyr Arg
        35                  40                  45

Gly Tyr Asn Pro Glu Asn Pro Asn Glu Pro Gly Asn Glu Met Asn Trp
50                  55                  60

Tyr Asp Ala Val Ala Gly Glu Ala Ser Pro Tyr Asp Asp Leu Ala His
65                  70                  75                  80

Gly Thr His Val Thr Gly Thr Met Val Gly Ser Glu Pro Asp Gly Thr
                85                  90                  95

Asn Gln Ile Gly Val Ala Pro Gly Ala Lys Trp Ile Ala Val Lys Ala
            100                 105                 110

Phe Ser Glu Asp Gly Gly Thr Asp Ala Asp Ile Leu Glu Ala Gly Glu
        115                 120                 125

Trp Val Leu Ala Pro Lys Asp Ala Glu Gly Asn Pro His Pro Glu Met
130                 135                 140

Ala Pro Asp Val Val Asn Asn Ser Trp Gly Gly Gly Ser Gly Leu Asp
145                 150                 155                 160

Glu Trp Tyr Arg Asp Met Val Asn Ala Trp Arg Ala Ala Asp Ile Phe
                165                 170                 175

Pro Glu Phe Ser Ala Gly Asn Thr Asp Leu Phe Ile Pro Gly Gly Pro
            180                 185                 190

Gly Ser Ile Ala Asn Pro Ala Asn Tyr Pro Glu Ser Phe Ala Thr Val
        195                 200                 205

Ala Thr Asp Ile Asn Lys Lys Leu Ala Asp Phe Ser Leu Gln Gly Pro
210                 215                 220

Ser Pro Tyr Asp Glu Ile Lys Pro Glu Ile Ser Ala Pro Gly Val Asn
225                 230                 235                 240

Ile Arg Ser Ser Val Pro Gly Gln Ala Tyr Glu Asp Gly Trp Asp Phe
                245                 250                 255

Thr Ser Met Ala Gly Pro His Val Ser Ala Val Ala Ala Leu Leu Lys
            260                 265                 270

Gln Ala Asn Ala Ser Leu Ser Val Asp Glu Met Glu Asp Ile Leu Thr
        275                 280                 285
```

```
Ser Thr Ala Glu Pro Leu Thr Asp Ser Thr Phe Pro Asp Ser Pro Asn
    290                 295                 300

Asn Gly Tyr Gly His Gly Leu Val Asn Ala Phe Asp Ala Val Ser Ala
305                 310                 315                 320

Val Thr Asp Gly Leu Gly Lys
                325
```